(12) United States Patent
Brongersma et al.

(10) Patent No.: US 7,939,024 B2
(45) Date of Patent: May 10, 2011

(54) SENSOR DEVICE COMPRISING ELONGATED NANOSTRUCTURES

(75) Inventors: Sywert H. Brongersma, Eindhoven (NL); Peter Offermans, Eindhoven (NL)

(73) Assignee: Stichting IMEC Nederland, Eindhoven (NL)

( * ) Notice: Subject to any disclaimer, the term of this patent is extended or adjusted under 35 U.S.C. 154(b) by 130 days.

(21) Appl. No.: 12/176,145

(22) Filed: Jul. 18, 2008

(65) Prior Publication Data
US 2009/0085071 A1 Apr. 2, 2009

Related U.S. Application Data

(60) Provisional application No. 60/951,857, filed on Jul. 25, 2007.

(30) Foreign Application Priority Data

Oct. 5, 2007 (EP) .................................... 07075865

(51) Int. Cl.
*G01N 27/00* (2006.01)
(52) U.S. Cl. ... 422/98; 422/68.1; 422/82.01; 422/82.02; 422/83; 438/48; 438/49; 436/43; 436/63; 977/902; 977/932; 977/953; 977/957; 977/958
(58) Field of Classification Search .................. 977/902, 977/932, 953, 957, 958; 422/68.1, 82.01, 422/82.02, 83, 98; 438/48, 49; 436/43, 63
See application file for complete search history.

(56) References Cited

U.S. PATENT DOCUMENTS

| 7,544,978 | B2 * | 6/2009 | Noy et al. ....................... 257/213 |
| 2002/0172820 | A1 * | 11/2002 | Majumdar et al. ............ 428/357 |
| 2002/0179434 | A1 | 12/2002 | Dai et al. |
| 2003/0134267 | A1 * | 7/2003 | Kang et al. ......................... 435/4 |
| 2005/0053525 | A1 | 3/2005 | Segal et al. |
| 2005/0064185 | A1 * | 3/2005 | Buretea et al. ................ 428/364 |
| 2005/0212014 | A1 * | 9/2005 | Horibe et al. .................. 257/213 |
| 2006/0052947 | A1 * | 3/2006 | Hu .................................... 702/20 |
| 2009/0075468 | A1 * | 3/2009 | Buretea et al. ................ 438/602 |
| 2009/0173976 | A1 * | 7/2009 | Augusto ........................ 257/292 |

OTHER PUBLICATIONS

Kong et al., Science, vol. 287, pp. 622-625 (Jan. 28, 2000).
Qi et al., "Toward Large Arrays of Multiplex Functionalized Carbon Nanotube Sensors for Highly Sensitive and Selective Molecular Detection" Nano Lett., vol. 3, No. 3, pp. 347-351 (2003).

(Continued)

*Primary Examiner* — Brian J Sines
(74) *Attorney, Agent, or Firm* — Knobbe Martens Olson & Bear LLP

(57) ABSTRACT

A sensor device is provided for determining the presence and/or amount of at least one component in a fluid. The sensor device comprises at least one sensor unit, the at least one sensor unit comprising at least one elongated nanostructure and a dielectric material surrounding the at least one elongated nanostructure. The dielectric material is such that it is selectively permeable for one of the at least one component and is capable of sensing the component permeated through the dielectric material. The sensor device according to preferred embodiments shows good sensitivity and good mechanical strength. The present invention furthermore provides a method for manufacturing such a sensor device and a method for determining the presence and/or amount of at least one component in a fluid using such a sensor device.

37 Claims, 13 Drawing Sheets

OTHER PUBLICATIONS

Drain et al., "A Perspective on Four New Porphyrin-Based Functional Materials and Devices" J. Porphyrins Phthalocyanines, 2002, 6, 241.

Fernández-Sánchez et al., "Novel optical $NO_2$-selective sensor based on phthalocyaninato-iron(II) incorporated into a nanostructured matrix", Sens. Actuators B, 2006, 113, 630.

* cited by examiner

SENSOR DEVICE COMPRISING ELONGATED NANOSTRUCTURES

CROSS-REFERENCE TO RELATED APPLICATIONS

This application claims the benefit under 35 U.S.C. §119 (e) of U.S. provisional application Ser. No. 60/951,857 filed on Jul. 25, 2007, and claims the benefit under 35 U.S.C. §119(a)-(d) of European application No. 07075865.1 filed on Oct. 5, 2007, the disclosures of which are hereby expressly incorporated by reference in their entirety and are hereby expressly made a portion of this application.

FIELD OF THE INVENTION

The present invention relates to sensor devices. More particularly, the present invention relates to a sensor device comprising at least one sensor unit comprising at least one elongated nanostructure, e.g. nanowire, embedded in a dielectric material, the dielectric material having a selective permeability towards a component to be detected in a fluid and the at least one elongated nanostructure having the capability of sensing the component permeated through the dielectric material. The present invention also relates to a method for manufacturing such a sensor device and to a method for determining the presence and/or amount of at least one component in a fluid using such a sensor device.

BACKGROUND OF THE INVENTION

Chemical sensors and biosensors have been utilized for detecting many species, from contaminants in air to the presence of particular DNA segments in blood samples or other samples. More recently, sensors utilizing nanostructures such as nanowires (NWs) and carbon nanotubes (CNTs) have been proposed. This has been described in detail in several papers such as in Kong et al., Science, vol. 287, pp. 622-625 (Jan. 28, 2000).

US 2005/0053525 describes sensor platforms and related methods of making such sensor platforms which comprise nanostructures such as nanowire sensor elements oriented substantially parallel with respect to a major surface of a substrate and having nanostructures, such as nanowires, which, in various embodiments, may have or may be formed to have an affinity for a corresponding analyte.

Furthermore chemical sensors have been described which are made of nanostructures which are functionalized or otherwise modified to become molecule-specific or species-specific sensors (see P. Qi et al., "Toward Large Arrays of Multiplex Functionalized Carbon Nanotube Sensors for Highly Sensitive and Selective Molecular Detection" Nano Lett., vol. 3, no. 3, pp. 347-51 (2003)).

Dai et al., "Carbon Nanotube Sensing," U.S. patent application Ser. No. 10/175,026, filed on Jun. 18, 2002, now U.S. Patent Publ. No. US-2002-0179434 A1.

Unfortunately, although sensor devices comprising nanostructures are described and capabilities are evolving for the use of individual nanotubes in a sensor arrangement, a need exists for a more reliable vehicle or platform, or in other words a more reliable design to serve as a sensor. The above-described devices are not reliable because they have limited selectivity and limited sensitivity especially at low concentrations.

SUMMARY OF THE INVENTION

A good sensor device for determining the presence and/or amount of at least one component in a fluid is desirable, as is a good method for manufacturing such a sensor device and a good method for determining the presence and/or amount of at least one component in a fluid using such a sensor device.

The sensor device according to preferred embodiments shows good sensitivity and good mechanical strength.

The sensor device can be used as a gas sensor for detecting at least one component in a gas or as a liquid sensor for detecting at least one component in a liquid.

In a first aspect, a sensor device is provided for determining the presence and/or amount of at least one component in a fluid. The sensor device comprises at least one sensor unit to be arranged in the fluid, the at least one sensor unit comprising at least one elongated nanostructure and a dielectric material essentially surrounding the at least one elongated nanostructure. The dielectric material is selectively permeable for one of the at least one component and the at least one elongated nanostructure is capable of sensing the component permeated through the dielectric material.

An advantage of a sensor device according to preferred embodiments is that it shows good selectivity and a good mechanical strength.

The at least one elongated nanostructure may have a bottom and a top, and the sensor device may furthermore comprise at least a first and second contact, the first contact being connected to the bottom of the at least one nanostructure and the second contact being connected to the top of the at least one nanostructure.

According to preferred embodiments, the sensor device may comprise at least two sensor units with elongated nanostructures having an essentially similar diameter and an essentially similar composition. With an essentially similar diameter is meant that the elongated nanostructures of the at least two sensor units have a diameter difference below 50% and preferably below 10%. With the term 'composition of the elongated nanostructures' is meant the material or combination of materials of which the elongated nanostructures are formed.

According to other preferred embodiments, the sensor device may comprise at least two sensor units with elongated nanostructures that differ from each other in composition and/or diameter.

According to preferred embodiments, the sensor device may comprise at least a first and second sensor unit, and the dielectric material surrounding the at least one elongated nanostructure of the first sensor unit may differ in composition. Alternatively or on top thereof, the thickness of the layer of dielectric material surrounding the at least one elongated nanostructure of the second sensor unit.

According to preferred embodiments, the first contact may be a drain contact and the second contact may be a source contact and the sensor device may comprise a gate structure underneath the drain contact.

The gate structure may comprise a gate contact and a gate dielectric, and the gate dielectric may be situated in between the gate contact and the drain contact such that the gate contact and the drain contact do not contact each other.

According to preferred embodiments, the at least first and second contacts may be formed of a conductive material such as e.g. a metal, an alloy, poly-Si, a metal silicide or a metal oxide.

The at least one elongated nanostructure may have a diameter of between 3 nm and 300 nm or a diameter lower than 100 nm, for example between 10 nm and 100 nm.

The at least one elongated nanostructure may be functionalized to improve selectivity to the component to be detected.

According to preferred embodiments, the at least one elongated nanostructure may be formed of a material selected from a group IV material such as silicon (Si), germanium (Ge), carbon (C) and binary compounds thereof, a III-V material such as InP, GaN, GaAs and binary, tertiary or quaternary compounds thereof, a II-IV material such as ZnSe and binary, tertiary and quaternary compounds thereof or a metal oxide.

The at least one elongated nanostructure may be a nanowire or a carbon nanotube.

According to preferred embodiments, the sensor device may furthermore comprise a detector for measuring a change in a physical property of the at least one elongated nanostructure upon adsorption of the at least one component in the nanostructure.

The detector may be an electrical detector for measuring a change in electrical conduction of the at least one nanostructure or may be an optical detector for measuring a change in electroluminescence of the at least one nanostructure.

In a further aspect, the use of the sensor device according to preferred embodiments as a gas sensor for detecting a gas molecule present in a gas is provided.

In still a further aspect, the use of the sensor device according to preferred embodiments as a liquid sensor for detecting a liquid molecule present in a liquid is provided.

In yet a further aspect, a method of manufacturing a sensor device for determining the presence and/or amount of at least one component in a fluid is provided. The method comprises providing at least one sensor unit. Providing at least one sensor unit comprises: providing at least one elongated nanostructure, and providing a dielectric material such that the at least one elongated nanostructure is essentially surrounded by the dielectric material, the dielectric material being selectively permeable for one of the at least one component and the at least one elongated nanostructure being capable of sensing the component permeated through the dielectric material.

Providing at least one elongated nanostructure may be performed by: providing a sacrificial layer, patterning the sacrificial layer so as to define at least one opening in the sacrificial layer, depositing a nanoparticle in each of the at least one opening in the sacrificial layer, removing the sacrificial layer, and growing at least one elongated nanostructure using the nanoparticle as a catalyst.

Providing at least one elongated nanostructure may comprise: electrochemically depositing at least one nanoparticle, and growing at least one elongated nanostructure using the nanoparticle as a catalyst.

According to preferred embodiments, the method may furthermore comprise functionalizing the at least one nanowire for improving its selectivity to the at least one component.

According to preferred embodiments, the method may furthermore comprise providing a detector for measuring a change in a property of the at least one elongated nanostructure upon adsorption of the at least one component in the nanostructure.

In a further aspect, a sensor device is provided for determining the presence and/or amount of at least one component in a fluid, the sensor device being obtained by a manufacturing method in accordance with preferred embodiments. The detector may be an electrical detector or an optical detector.

In yet a further aspect, a method is provided for determining the presence and/or amount of at least one component in a fluid. The method comprises: providing the fluid comprising the at least one component to a sensor device, the sensor device comprising at least one sensor unit, the at least one sensor unit comprising at least one elongated nanostructure and a dielectric material surrounding the at least one elongated nanostructure, the dielectric material being selectively permeable for one of the at least one component, allowing the at least one component to penetrate through the dielectric material and adsorb to the at least one elongated nanostructure, measuring a change in a property of the at least one elongated nanostructure, and from this change determining the presence and/or amount of the at least one component in the fluid.

According to preferred embodiments, providing the fluid comprising the at least one component to the sensor device may be performed by providing a gas comprising at least one gas molecule to be detected.

According to other preferred embodiments, providing the fluid comprising the at least one component to the sensor device may be performed by providing a liquid comprising at least one liquid molecule to be detected.

According to preferred embodiments, measuring a change in a property of the at least one elongated nanostructure may be performed by measuring a change in electrical conduction of the at least one elongated nanostructure.

According to other preferred embodiments, measuring a change in a property of the at least one elongated nanostructure may be performed by measuring a change in electroluminescence of the at least one elongated nanostructure.

Particular and preferred aspects are set out in the accompanying independent and dependent claims. Features from the dependent claims may be combined with features of the independent claims and with features of other dependent claims as appropriate and not merely as explicitly set out in the claims.

Although there has been constant improvement, change and evolution of devices in this field, the present concepts are believed to represent substantial new and novel improvements, including departures from prior practices, resulting in the provision of more efficient, stable and reliable devices of this nature.

The above and other characteristics, features and advantages of the preferred embodiments will become apparent from the following detailed description, taken in conjunction with the accompanying drawings, which illustrate, by way of example, the principles of the invention. This description is given for the sake of example only, without limiting the scope of the invention. The reference figures quoted below refer to the attached drawings.

Figure 1:
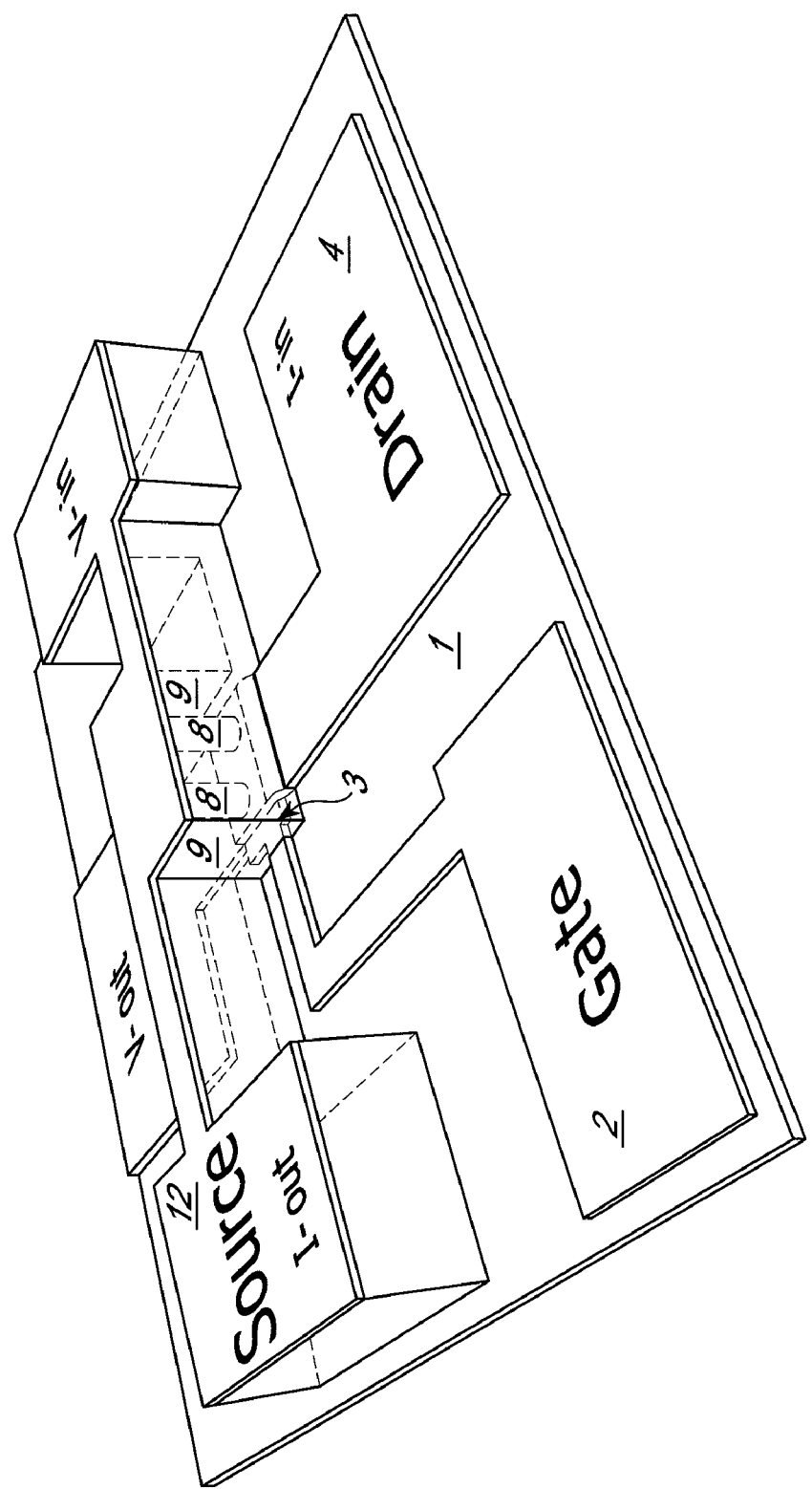
FIG. 1 shows a top view of a sensor device according to preferred embodiments.
Figure 2:
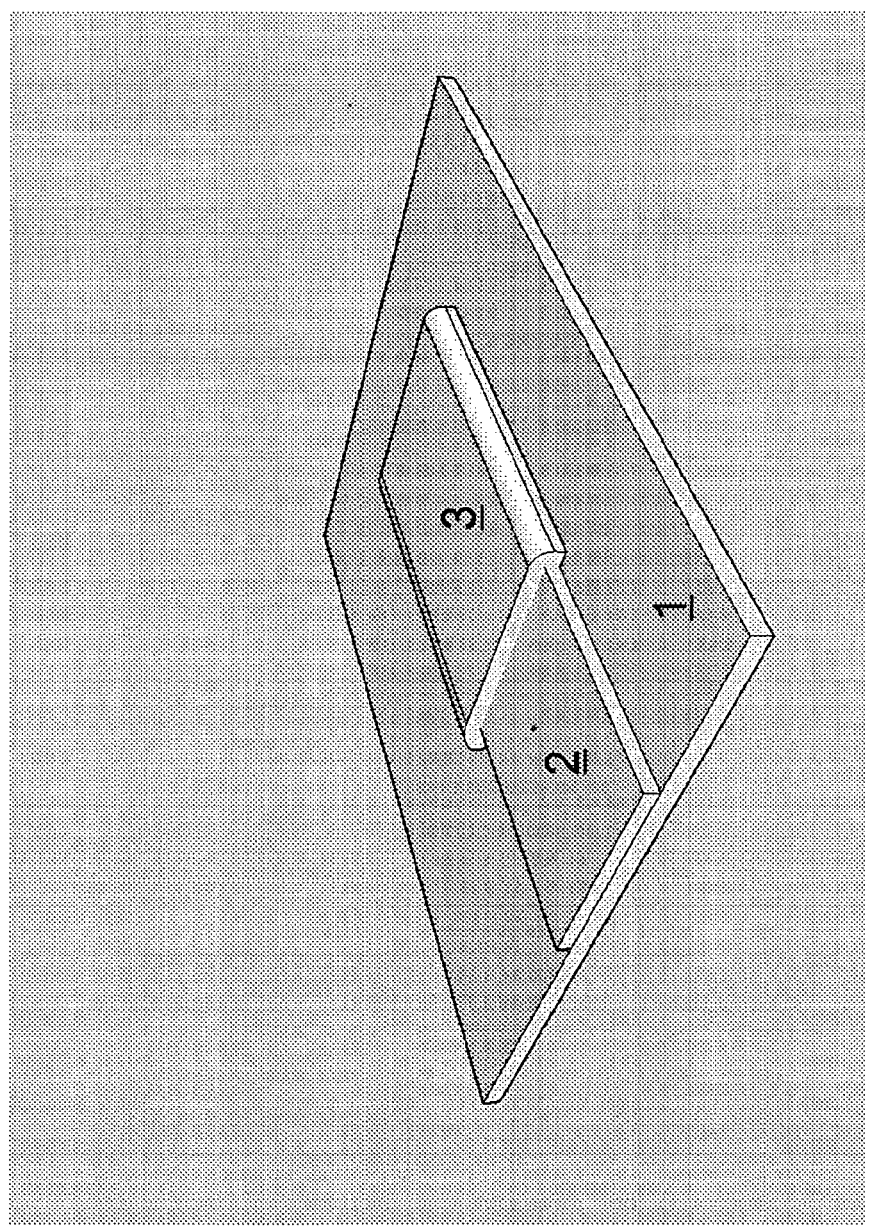
FIG. 2 to FIG. 12 illustrate subsequent steps in a method according to preferred embodiments.

In the different figures, the same reference signs refer to the same or analogous elements.

DETAILED DESCRIPTION OF THE PREFERRED EMBODIMENT

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Moreover, the terms top, over and the like in the description and the claims are used for descriptive purposes and not necessarily for describing relative positions. It is to be understood that the terms so used are interchangeable under appropriate circumstances and that the preferred embodiments described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary preferred embodiments, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that preferred embodiments may be practiced without these specific details. In other instances, well-known methods, structures and techniques have not been shown in detail in order not to obscure an understanding of this description.

The following terms are provided solely to aid in the understanding of the invention.

With the term "functionalization" of elongated nanostructures is meant surface functionalization of the elongated nanostructure such as the introduction of chemical functional groups to the surface of the nanostructure.

The terms "nanowire sensor device", "sensor device" and "detection system comprising elongated nanostructures" refer to the same system or device. The device can comprise several sensor units connected to each other.

The invention will now be described by a detailed description of several preferred embodiments. It is clear that other preferred embodiments can be configured according to the knowledge of persons skilled in the art without departing from the true spirit or technical teaching of the invention, the invention being limited only by the terms of the appended claims.

A sensor device, also referred to as detecting system, is provided for determining the presence and/or amount of at least one component in a fluid, e.g. liquid or gas, a method for forming such a sensor device, a sensor device obtained by such a method, and a method for determining the presence and/or amount of at least one component in a fluid using such a device. The fluid may be a liquid or a gas.

In a first aspect, a sensor device is provided for determining the presence and/or amount of at least one component in a fluid. The sensor device comprises at least one sensor unit, the at least one sensor unit comprising at least one elongated nanostructure and a dielectric material surrounding the at least one elongated nanostructure. The dielectric material is selectively permeable for one of the at least one component to be detected.

The sensor device according to preferred embodiments comprises at least one elongated nanostructure which is embedded in a dielectric material. The dielectric material is selectively permeable for or, in other words, is selectively penetrable by the at least one component to be detected, e.g. a selection of gasses and/or liquids. Because of the selective permeability of the dielectric material, the fluid, e.g. gasses and/or liquids can reach the at least one elongated nanostructure such that it can be detected and/or measured. The elongated nanostructures may be functionalized to enhance their selectivity with respect to the component to be detected (see further).

By properly choosing the dielectric material control can be obtained over the components that will be able to penetrate through the dielectric material. Hence, control over the selectivity of the sensor device can be obtained.

The sensor device according to preferred embodiments can be a field-effect transistor (FET) and may comprise at least one first contact and at least one second contact, respectively at least one source and at least one drain contact. Additionally, the FET may comprise a gate structure.

Hereinafter, the sensor device according to preferred embodiments will described by means of a FET. It has to be understood that this is only for the ease of explanation and that this is not intended to limit the invention in any way. Furthermore, the sensor device according to preferred embodiments will be described with reference to nanowires and nanowire sensor devices. It has to be understood that this is not intended to limit the invention in any way. Whenever the terms "nanowire" or "nanowires" are mentioned in the description, this is to be read and understood as the more general terminology "elongated nanostructure". With the term "elongated nanostructures" is meant any two-dimensionally confined pieces of solid material in the form of wires (nanowires), tubes (nanotubes), rods (nanorods) and similar elongated substantially cylindrical or polygonal nanostructures having a longitudinal axis. A cross-dimension of the elongated nanostructures preferably lies in the range of 1 nm to 500 nm, in the range of 3 nm to 300 nm, or below 100 nm. According to preferred embodiments, organic elongated nanostructures, such as e.g. carbon nanotubes (CNTs), or inorganic elongated nanostructures, such as e.g. semiconducting nanowires (e.g. silicon nanowires) may be used. Furthermore, whenever the term "nanowire sensor device" is used, this is to be understood as a sensor device comprising at least one elongated nanostructure.

FIG. 1 shows a top view of a FET nanowire sensor device 20 according to an embodiment. The sensor device 20 is provided for determining the presence and/or the amount of one or more specific components that are present in a fluid. The fluid may be a gas or a liquid, while the component to be detected may also be a gas or a fluid. The nanowire sensor device 20 is formed on a substrate 1 and comprises one sensor unit. It has to be understood that although the shown embodiment has one sensor unit, this is not intended to limit the invention in any way. The sensor device 20 according to other preferred embodiments may comprise more sensor units. They can in fact comprise any number of sensor units required for a particular application.

In the embodiment shown in FIG. 1, the nanowire sensor device 20 comprises two elongated nanostructures 8 embedded in or, in other words, surrounded by a dielectric material 9. The dielectric material is chosen to be selectively permeable for one or more components to be detected in a fluid. Because of the selective permeability towards one or more components to be detected, i.e. the ability of the dielectric material 9 to transmit certain pre-determined fluids comprising these components to be detected, only these components will be able to reach the nanowires 8 embedded in the dielectric material 9 and thus only these components will be detected by the nanowires 8 (see further). It has to be understood that the nanowire sensor device 20 of FIG. 1 is shown only for illustration purposes only. The nanowire sensor device 20 according to preferred embodiments may comprise any number of nanowires 8 as required for a particular application.

The nanowire sensor device 20 illustrated in FIG. 1 is based on a "gate beyond drain" principle. The nanowires 8 define a longitudinal axis and a bottom and a top located at either side along their longitudinal axis. The nanowire sensor device 20 of FIG. 1 has a drain contact 4 connected to the bottom of the nanowires 8 and a source contact 12 connected to the top of the nanowires 8. The sensor device 20 furthermore comprises a gate contact 2 connected to the bottom of the nanowires 8 and separated from the drain contact 4 by a gate dielectric 3, such that the drain contact 4 and the gate contact 2 are not in direct contact with each other. The gate contact 2 and gate dielectric 3 may be referred to as gate structure. However, it has to be clear that alternative configurations are also possible. For example, according to alternative preferred embodiments, the source contact 12 may be connected to the bottom of the nanowires 8 and the gate and drain contacts 2, 4 may be connected to the top of the nanowires 8. According to other embodiments, the sensor device 20 may even not have a gate structure. In this case the sensor device 20 may comprise a first, e.g. drain, contact 4 and a second, e.g. source, contact 12, without gate contact. According to still further preferred embodiments, the substrate 1 may act as a source contact and the nanowires 8 are in direct contact with the substrate 1.

In the nanowire sensor device 20 as illustrated in FIG. 1, the nanowires 8 are provided on the drain contact 4. The nanowires 8 may have a longitudinal axis. When the main surface 1a of the substrate 1 defines a plane, the respective longitudinal axis of each nanowire 8 extends in a direction substantially perpendicular to this plane. Furthermore, the longitudinal axis of the nanowires 8 may be substantially parallel to each other. The dielectric material 9 the nanowires 8 are surrounded with or, in other words, embedded in, may be a porous dielectric material 9. According to preferred embodiments, the dielectric material 9 may be an optically transparent dielectric material. The second contact 12, in the example given the source contact, may, according to the present example, be located on top of the dielectric material 9.

By properly choosing the dielectric material 9 the selectivity of the sensor device 20 according to preferred embodiments can be controlled. Control can be obtained by tuning the properties of the dielectric material 9, i.e. which components are allowed penetrating through the dielectric material 9 and which are not. In case of porous material, this may for example be obtained by tuning the porosity and/or the pore size in the dielectric material 9.

According to preferred embodiments, the nanowires 8 may be functionalized, i.e. additional functionality may be incorporated in the nanowires 8, in order to improve their selectivity to the components to be detected in the fluid. The functionalization may be performed either after growing the nanowires 8 but before embedding them in the dielectric material 9 or after the entire integration approach, i.e. after growing the nanowires 8 and providing the dielectric material 9. The choice depends on how susceptible the functionalization process is to subsequent process steps and how easily the functionalization process can be performed while the nanowires 8 are embedded in the dielectric material 9.

According to preferred embodiments, the nanowires 8, or, more generally, the elongated nanostructures, may be functionalized by modification of their surface by, for example, chemical modification, physical adsorption of molecules at their surface, metallization or a combination thereof. Chemical modification of nanowires 8 may, as known by a person skilled in the art, comprise grafting molecules to the nanowires 8 by e.g. plasma treatment or chemical treatment. The chemical modification of the nanowires 8, or, more generally, the elongated nanostructures, may involve the use of radical precursor molecules able to be grafted in a covalent way to the nanowires 8. According to other embodiments, commercially available functionalized nanowires 8, or in general elongated nanostructures, may also be used. For example, amino-, hydroxyl-, carboxylic acid-, thiol-functionalized nanowires 8 may be used.

Functionalization of the nanowires 8 may, according to preferred embodiments, be done with redox-active molecules such as, for example, porphyrins or phthalocyanines. Complexation with electron accepting or electron donating gas molecules (e.g. $NO_2$, $NH_3$) may then lead to dipole formation at a surface or charge transfer to a channel of the sensor device 20, which can then electrically be detected. Such processes are described in "A Perspective on Four New Porphyrin-Based Functional Materials and Devices" J. Porphyrins Phthalocyanines, 2002, 6, 241, by C. M. Drain et al and in "Novel optical $NO_2$-selective sensor based on phthalocyaninato-iron(II) incorporated into a nanostructured matrix", Sens. Actuators B, 2006, 113, 630 by J. F. Fernandez-Sanchez et al.

The second contact, in the example given source contact 12, may be in direct contact with the nanowires 8. The nanowires 8 in turn may be in direct contact with the first contact, in the example given above the drain contact 4. Hence, the nanowires 8 may be located in between and in direct contact with the first and second contact, in the example given with the drain and source contacts 4, 12. In this way, in case the nanowire sensor device 20 according to preferred embodiments is used as a test device for characterizing or testing usability of the nanowires 8 when used in sensor devices, rapid evaluation of a variety of nanowires 8 in the as-grown position can be performed, either by four-point resistivity or device characterization. Hence, for these test purposes, no complete devices have to be built, which reduces testing time.

The sensor device 20 may also comprise a detector 13 for measuring a change in a physical property of the at least one nanowire 8 upon adsorption of the at least one component to be detected to the at least one nanowire 8. According to preferred embodiments, the detector 13 may be an electrical detector for measuring a change in electrical conduction of the at least one nanostructure upon adsorption of the at least on component to the at least one nanowire 8. According to other preferred embodiments, the detector 13 may be an optical detector for measuring a change in electroluminescence of the at least one nanostructure upon adsorption of the at least one component to the at least one nanowire 8.

A sensor device 20 according to other preferred embodiments comprises a plurality of sensor units, each sensor unit comprising at least one nanowire 8 embedded in a dielectric material 9 which selectively allows penetrating of a component to be detected. According to preferred embodiments, the individual sensor units comprise similar nanowires 8. With similar nanowires 8 is meant nanowires 8 formed of similar material and having a similar diameter. A diameter is construed to be similar to another diameter if both diameters do not differ by more than 50%. In a more strict interpretation, the word similar means that the diameters do not differ by more than 10%.

According to other preferred embodiments, the sensor units may each comprise different nanowires 8, i.e. nanowires 8 which may differ in diameter and/or composition. The term composition of the elongated nanostructures is meant to indicate the material or combination of materials of which the elongated nanostructures 8 are formed. The sensor device 20 according to the latter embodiments allows determining the presence and/or amount of different components in the same fluid.

According to preferred embodiments individual sensor units can be combined such that the diffusion distances of particular components through the dielectric material 9 towards the nanowires 8 are varied such that the penetration velocity or diffusion distances of the components becomes an important parameter to distinguish between different components. Selectivity may be set by combining several units each having a different diffusion distance, so that a range is available of required diffusion distances before the corresponding nanowire 8 is reached. Consequently, not only the nanowire sensitivity itself is important, but also the diffusion velocity through the dielectric material 9 may play an important role and differences in diffusion velocities may be exploited during a same measurement.

The sensor device 20 according to preferred embodiments provides specificity for a particular component to be detected in a fluid, by a combination of one or more approaches. The nanowire material can be chosen such that it is sensitive to the specific compounds to be detected. Furthermore, the nanowire material can be functionalized, as described above. Thirdly, the dielectric material 9 in which the nanowires 8 are embedded can be chosen to only allow penetrating of the component to be detected. Moreover, a porous dielectric material 9 can be chosen and porosity and size of pores can be chosen so as to improve selectivity. Finally, by providing a sensor device 20 comprising a plurality of sensor units, diffusion velocity of components can be measured and used to identify the respective components.

The sensitivity of the sensor device 20 according to preferred embodiments can be set by altering, i.e. by increasing or decreasing, the number and/or diameter of the nanowires 8 per sensor unit.

Also provided is a method for determining the presence and/or amount of at least one component in a fluid. The method comprises: providing a fluid, e.g. gas or liquid, comprising the at least one component to a sensor device 20, the sensor device 20 comprising at least one sensor unit, the at least one sensor unit comprising at least one elongated nanostructure 8 and a dielectric material 9 surrounding the at least one elongated nanostructure 8, the dielectric material 9 being selectively permeable for at least one of the at least one component to be detected, allowing the at least one component to penetrate through the dielectric material 9 and adsorb to the at least one elongated nanostructure 8, measuring a change in a property of the at least one elongated nanostructure 8, and from the change caused by the adsorption of the at least one component determining the presence and/or amount of the at least one component in the fluid.

For the ease of explanation, the method for determining the presence and/or amount of a particular component in a fluid according to preferred embodiments will be described by means of a sensor device 20 comprising nanowires 8. Again, this is not intended to limit the invention in any way and the method may be applied to any sensor device 20 comprising elongated nanostructures 8 embedded in, or in other words surrounded by a dielectric material 9 which is selectively permeable with respect to the particular component to be detected in a fluid.

As already mentioned above, the sensor device 20 may be a gas sensor device for detecting components, i.e. particular gas molecules, in a gas or may be a liquid sensor device for detecting components, i.e. particular liquid molecules, in a liquid.

In case of a gas sensor device 20, also referred to as a gas sensitive detector, only those gas molecules that can penetrate through the dielectric material 9 in which the nanowires 8 are embedded will be able to reach the nanowires 8. Hence, only the gas molecules for which the dielectric material 9 of the sensor device 20 is permeable will be detected by the nanowires 8 because, when reaching the nanowires 8, the gas molecules will induce a change in the electrical conduction of the nanowires 8 by adsorbing to the nanowires 8. The change in electrical conduction will depend on the number of gas molecules reaching the nanowires 8 and thus may be a measure for the concentration of that particular gas molecule in the total gas phase. Instead of an electrical gas sensor device 20, in which detection of the gas molecules is performed by a change in electrical conduction of the nanowires 8 as described above, the gas sensor device 20 may be an optical gas sensor device in which a change in electroluminescence of the nanowires 8 is detected when the gas molecules to be detected reach the nanowires 8 and adsorb to them.

In case of liquid sensor device 20, also referred to as a liquid sensitive detector, only those liquid molecules that can penetrate through the dielectric material 9 in which the nanowires 8 are embedded will be able to reach the nanowires 8. Hence, only the liquid molecules for which the dielectric material 9 of the sensor device 20 is permeable will be detected by the nanowires 8 because, when reaching the nanowires 8, the liquid molecules will induce a change in the electrical conduction of the nanowires 8 by adsorbing to the nanowires 8. This change in electrical conduction depends on the number of the liquid molecules of interest that can reach the nanowires 8 and may thus be a measure for the relative concentration of those particular liquid molecules in the liquid. As an alternative to an electrical liquid sensor device 20 wherein a change in electrical conduction of the nanowires 8 is measured for detecting the liquid molecules, the sensor device 20 may be an optical liquid sensor device in which liquid molecules are detected by measuring a change in electroluminescence of the nanowires 8 when the liquid molecules to be detected reach the nanowires 8 and adsorb to them.

For example, when a liquid sensor device 20 is used for determining molecules which are dissolved in a solvent or in a mixture of solvents, the sensor device 20 may be constructed such that it is sensitive to the dissolved molecules, in other words, the nanowires 8 in the sensor device 20 may be embedded in a dielectric material 9 which is selectively permeable with respect to the dissolved molecules. Hence, only the dissolved molecules to be detected in the liquid will be able to penetrate through the dielectric material 9 and will thus be able to reach the nanowires 8 and produce a change in the properties of the nanowires 8, e.g. a change in electrical conduction or electroluminescence. This change in properties, e.g. electrical conduction or electroluminescence, depends on the number of molecules dissolved in the solvent and thus will depend on the number of molecules able to reach the nanowires 8 and may thus be a measure for the concentration of that particular dissolved molecule present in the solvent.

In order to determine several different components in a same fluid, e.g. in a same liquid or gas, the sensor device 20 may comprise several individual sensor units, each unit comprising at least one nanowire 8 embedded in a dielectric material 9. The pieces of dielectric material 9 of the different units may be different from each other, may be similar or may be identical, and may be selectively permeable to other components. The sensor device 20 according to preferred embodiments may comprise any suitable number of sensor units as is required for a particular application. The number of sensor units present in a sensor device 20 according to preferred embodiments may depend on the number of different components to be detected in a fluid, e.g. in a gas or liquid.

Furthermore a method is provided for the manufacturing of a sensor device 20 for detecting at least one component in a fluid as described above. The method comprises providing one or more sensor units. Providing a sensor unit comprises: providing at least one elongated nanostructure 8, and providing a dielectric material 9 such that the at least one elongated nanostructure 8 is surrounded by the dielectric material 9, the dielectric material 9 being selectively permeable for one of the at least one component.

Hereinafter, subsequent steps in a method according to preferred embodiments will be described. It has to be understood that this description is not intended to limit the invention in any way and that the method may comprise more or fewer steps or may comprise a different sequence of steps or may involve the use of other materials.

Subsequent steps of a method according to preferred embodiments for the manufacturing of a sensor device 20 will be described by means of FIG. 2 to FIG. 12 for the manufacturing of a FET transistor as described with respect to the first embodiment. The method illustrates manufacturing of a sensor device 20 comprising one sensor unit. It has to be understood that the method according to preferred embodiments may also be applied for manufacturing sensor devices 20 comprising any number of sensor units required for a particular application.

In a first step, a substrate 1 is provided. The substrate 1 may comprise any suitable material known by a person skilled in the art. In preferred embodiments, the term "substrate" may include any underlying material or materials that may be used, or upon which a device, a circuit or an epitaxial layer may be formed. In other alternative embodiments, this "substrate" may include a semiconductor substrate such as e.g. doped silicon, a gallium arsenide (GaAs), a gallium arsenide phosphide (GaAsP), an indium phosphide (InP), a germanium (Ge), or a silicon germanium (SiGe) substrate. The "substrate" may include for example, an insulating layer such as a $SiO_2$ or a $Si_3N_4$ layer in addition to a semiconductor substrate portion. Thus, the term substrate also includes silicon-on-glass, silicon-on sapphire substrates. The term "substrate" is thus used to define generally the elements for layers that underlie a layer or portions of interest. Also, the "substrate" may be any other base on which a layer is formed, for example a glass or metal layer. Examples of suitable substrates 1 which may be used with preferred embodiments may be silicon and/or germanium comprising substrates (e.g. Ge, Si, SiGe, $SiO_2$, SiC), an SOI (silicon-on-insulator) or GOI (germanium-on-insulator) substrate or a (flexible) substrate made of a polymeric (e.g. plastic) material such as a polyimide sheet.

Figure 3:
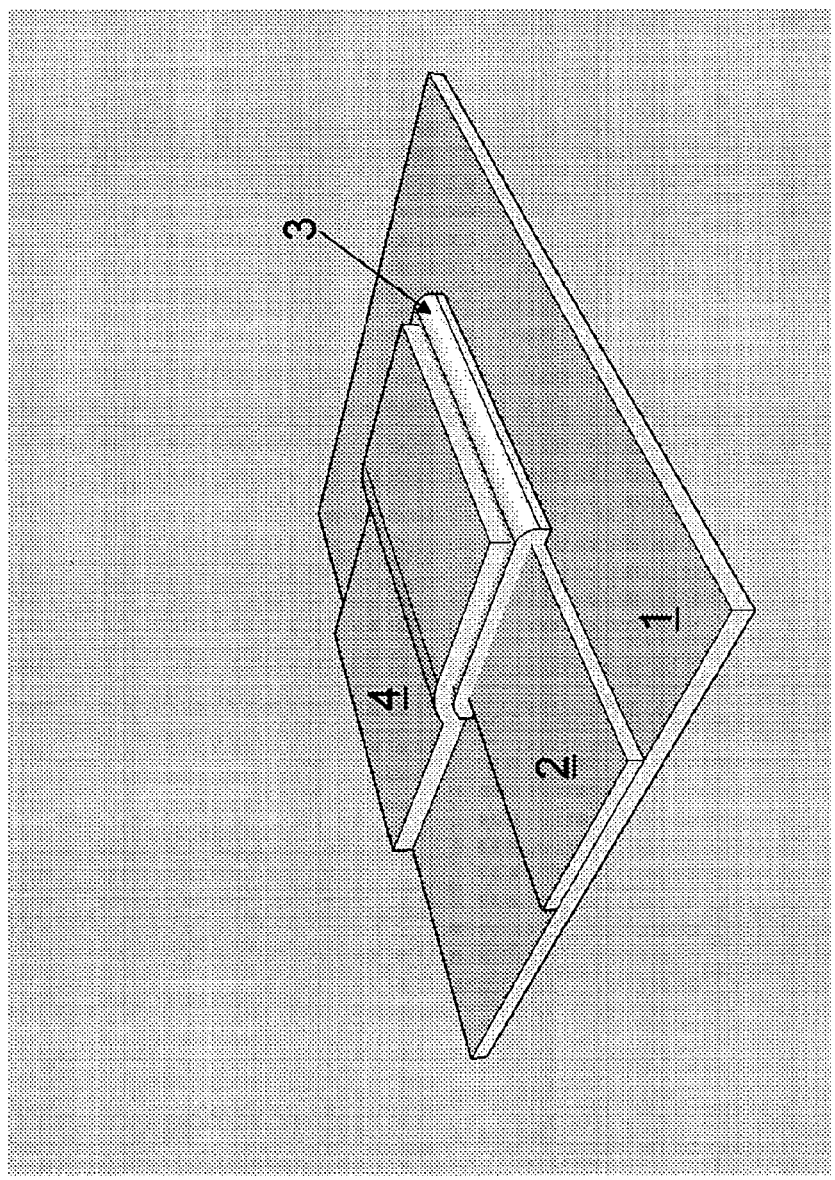

Onto the substrate 1 a gate structure comprising a gate contact 2 and a gate dielectric 3 may be provided. The gate contact 3 may be formed of a conductive material such as a metal, a metal oxide, an alloy, Si, poly-Si or a metal silicide. The material of the drain contact 4 may be chosen such that, when nanowires 8 are grown onto it (see further), a Schottky contact is formed between the nanowires 8 and the drain contact 4. A preferred material used in state of the art methods to form drain contacts may be Pt. However, this shows poor adhesion to dielectric materials. Therefore, according to preferred embodiments, materials such as TiN may be used. The gate dielectric 3 may be provided onto the gate contact 2 (see FIG. 2). The gate dielectric 3 may be formed of a commonly used dielectric material and may, for example, be a high-k material such as e.g. $HfO_2$. Onto the gate dielectric 3 a drain contact 4 may be formed as is illustrated in FIG. 3. This may be done by any suitable technique known by a person skilled in the art. The drain contact 4 may be formed of a conductive material such as e.g. a metal, a metal oxide, an alloy, Si, poly-Si or a silicide. The gate dielectric 3 may be located in between the drain contact 4 and the gate contact 2 and is such that the gate contact 2 and the drain contact 4 do not make direct contact to each other.

Figure 4:
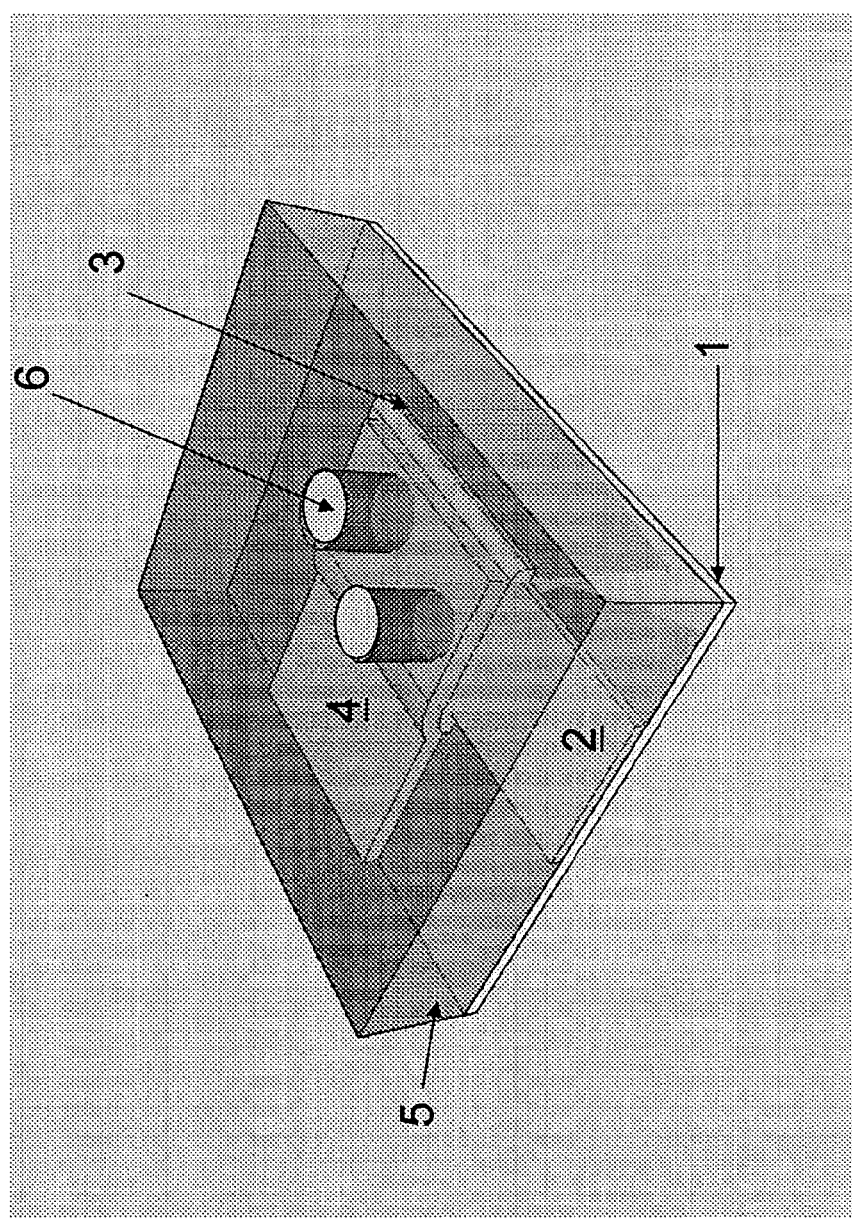

In a next step which is illustrated in FIG. 4, a sacrificial layer 5 may be provided over the drain contact 4. The sacrificial layer 5 may be patterned so as to define at least one opening 6 located above part of the drain contact 4 that is above the gate contact 2. The sacrificial layer 5 may, for example, comprise a spin-on material, such a e.g. a BARC (Bottom Anti-Reflective Coating) material, SiLK®, a polyarylsulfone, a polyhydroxystyrene based derivative, a polyimide, a polyether (e.g. polyarylene ethers e.g. FLARE® obtainable from Honeywell or VELOX® obtainable from Schumacher), a polyarylenesulfide, a polycarbonate, an epoxy, an epoxyacrylate, a polyarylene (e.g. a polyphenylene), a polyarylenevinylene (e.g. a polyphenylenevinylene), a polyvinylcarbazole, a cyclic olefin, and/or a polyester. Patterning of the sacrificial layer 5 may be done by any suitable technique known by a person skilled in the art, such as e.g. lithographic techniques. Lithographic patterning may be performed by, for example, optical lithography (including immersion lithography), electron-beam lithography or X-ray lithography. The lithographic patterning may comprise additional steps of e.g. depositing extra layers such as photosensitive layers (e.g. resists) and/or anti-reflective coatings, or may comprise removing remaining layers after patterning (e.g. resist stripping) or dry-etching the pattern in the sacrificial layer 5. Alternatively, the sacrificial layer 5 may act as a photosensitive layer or as an anti-reflective coating itself such that the amount of additional steps can be reduced.

Figure 5:
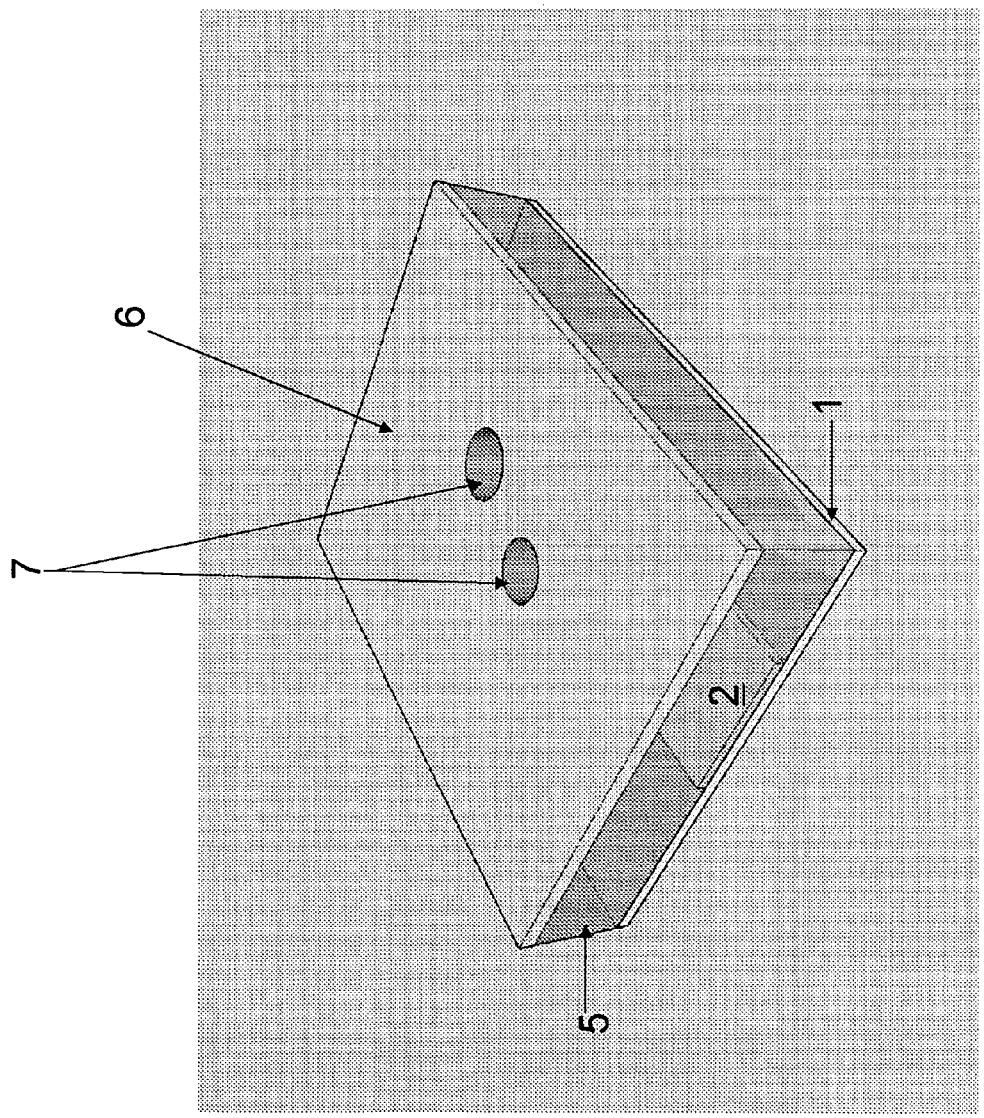
Figure 6:
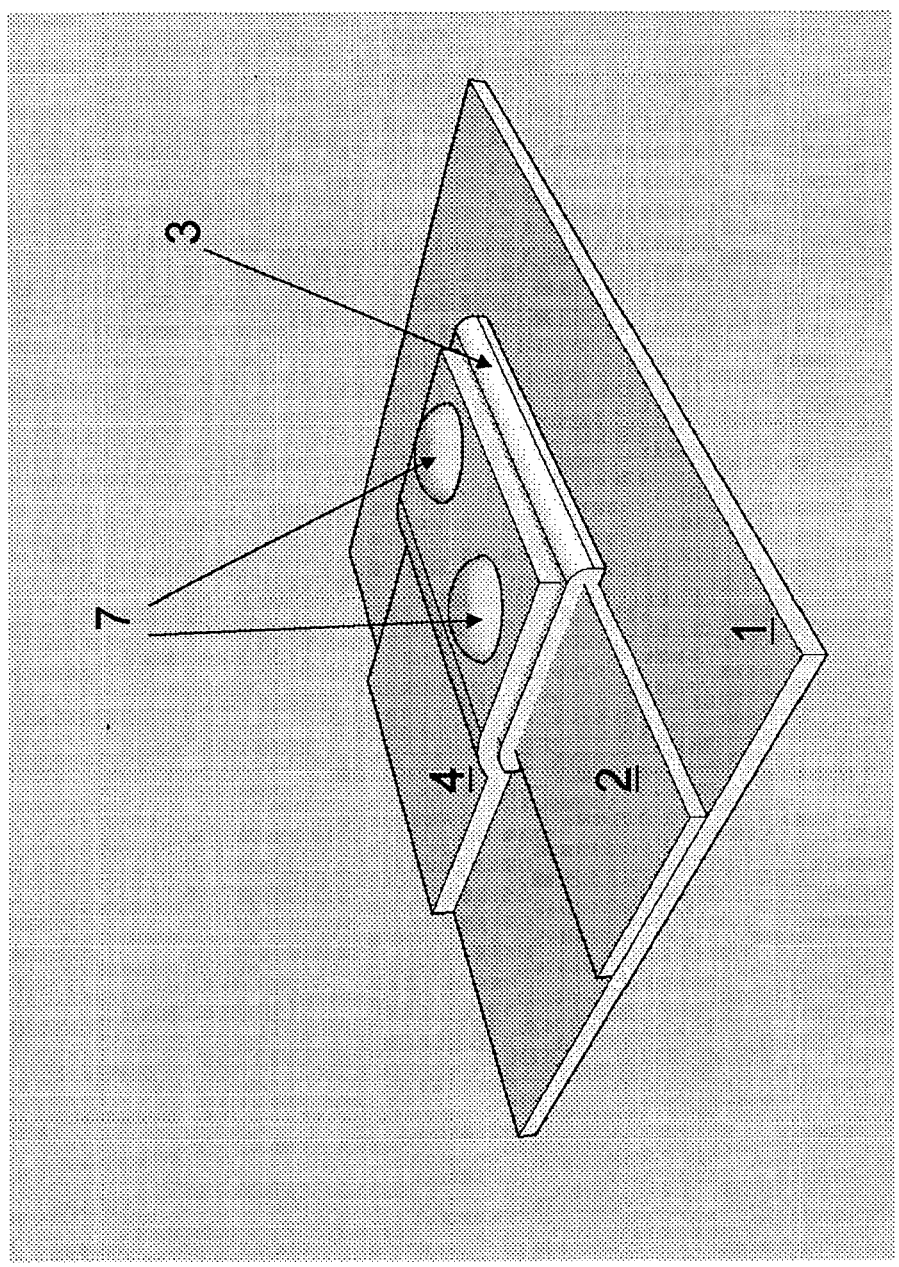

In a next step, illustrated in FIG. 5, catalyst nanoparticles 7 for initiating nanowire growth may provided in the holes 6 in the sacrificial layer 5. Therefore, a thin layer of catalyst material may be deposited over the sacrificial layer 5. The catalyst material may be any suitable catalyst material known by a person skilled in the art and may, for example, be a conductive material such as a metal, a semiconductive material such as silicon, or may be SiO. A subsequent removal, e.g. by lift-off processes such as wet etching and/or dry back etching of the sacrificial layer 5, leaves the catalyst material only in the area(s) wherein the nanowires 8 are expected to be provided. In that way, nanowires 8 can be grown at predetermined locations. This implies that all lithographical critical steps have been performed before the nanowires 8 are grown and thus the nanowires 8 formed cannot be damaged anymore during further processing. To create catalytic nanoparticles 7 with a diameter smaller than the diameter of the openings 6 in the sacrificial layer 5, an additional annealing step may be performed to break up the particles 7 in particles with a smaller diameter. The diameter of the nanoparticles 7 determines the diameter of the nanowires 8 grown by using these nanoparticles 7. In FIG. 6 the structure obtained up till now and comprising selectively deposited catalyst nanoparticles 7 is illustrated.

According to alternative embodiments, catalyst nanoparticles 7 may be provided in different ways. For example, according to a first alternative, an upper surface of the drain contact 4 is used as a catalyst in nanowire growth. A material suitable to be used in that case may be silicon. According to another alternative, selective deposition techniques such as e.g. electrochemical deposition (ECD) may be used to selectively deposit nanoparticles 7 at predetermined locations. In the above-discussed example, thereafter nanoparticles 7 are deposited on top of the drain contact 4. According to a further alternative method, catalyst nanoparticles 7 may be provided by first depositing a thin film of catalyst material on the drain contact 4 and subsequently etching this thin film to form the nanoparticles 7. According to these alternative methods, the provision of a sacrificial layer 5 is not required and thus may be omitted.

Again, it has to be understood, that according to alternative preferred embodiments and as already mentioned above, a source contact 12 may be provided at the bottom of the nanowires 8, i.e. closest to the substrate 1 on which the sensor device 20 is formed and a drain contact 4 may be provided at the top of the nanowires 8, i.e. furthest away from the substrate 1 on which the sensor device 20 is formed. In that case, nanoparticles 7 may be provided onto the source contact 12 instead of onto the drain contact 4 as described above.

Figure 7:
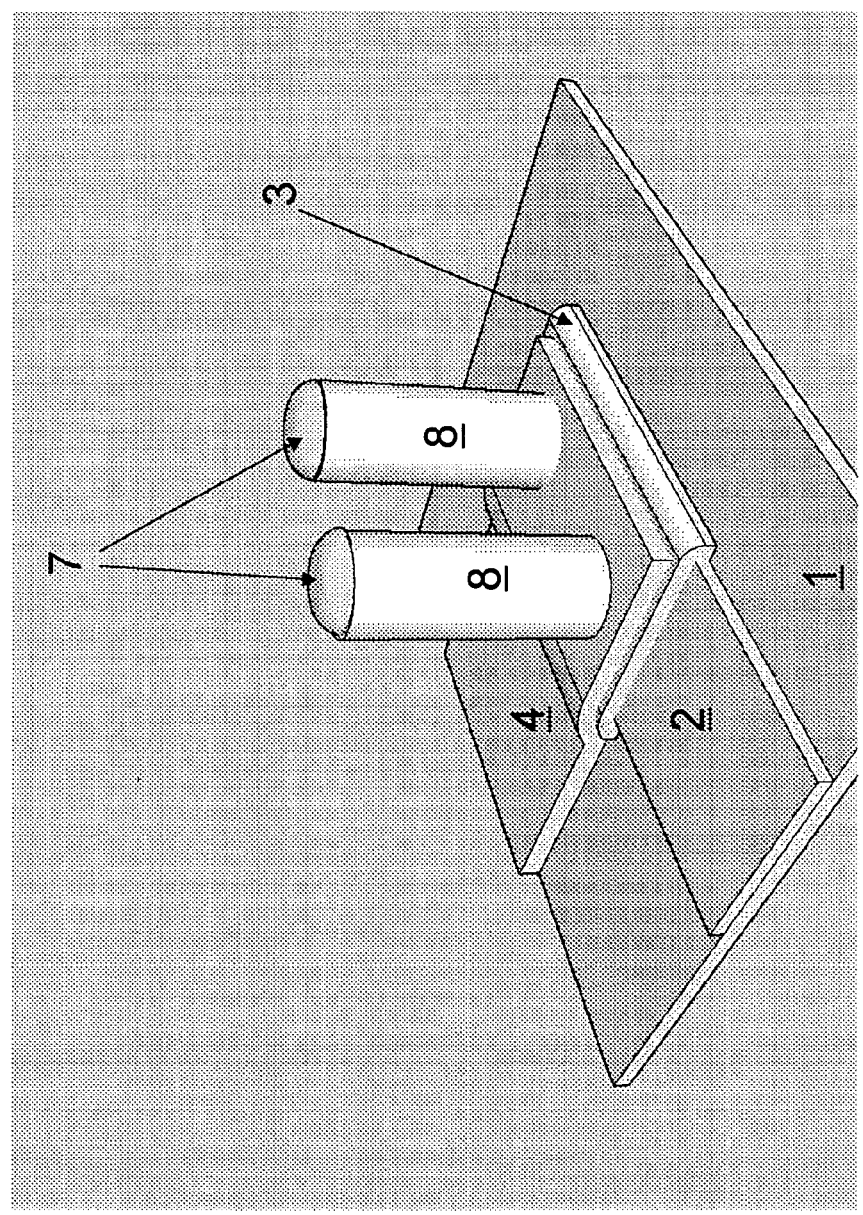
Figure 8:
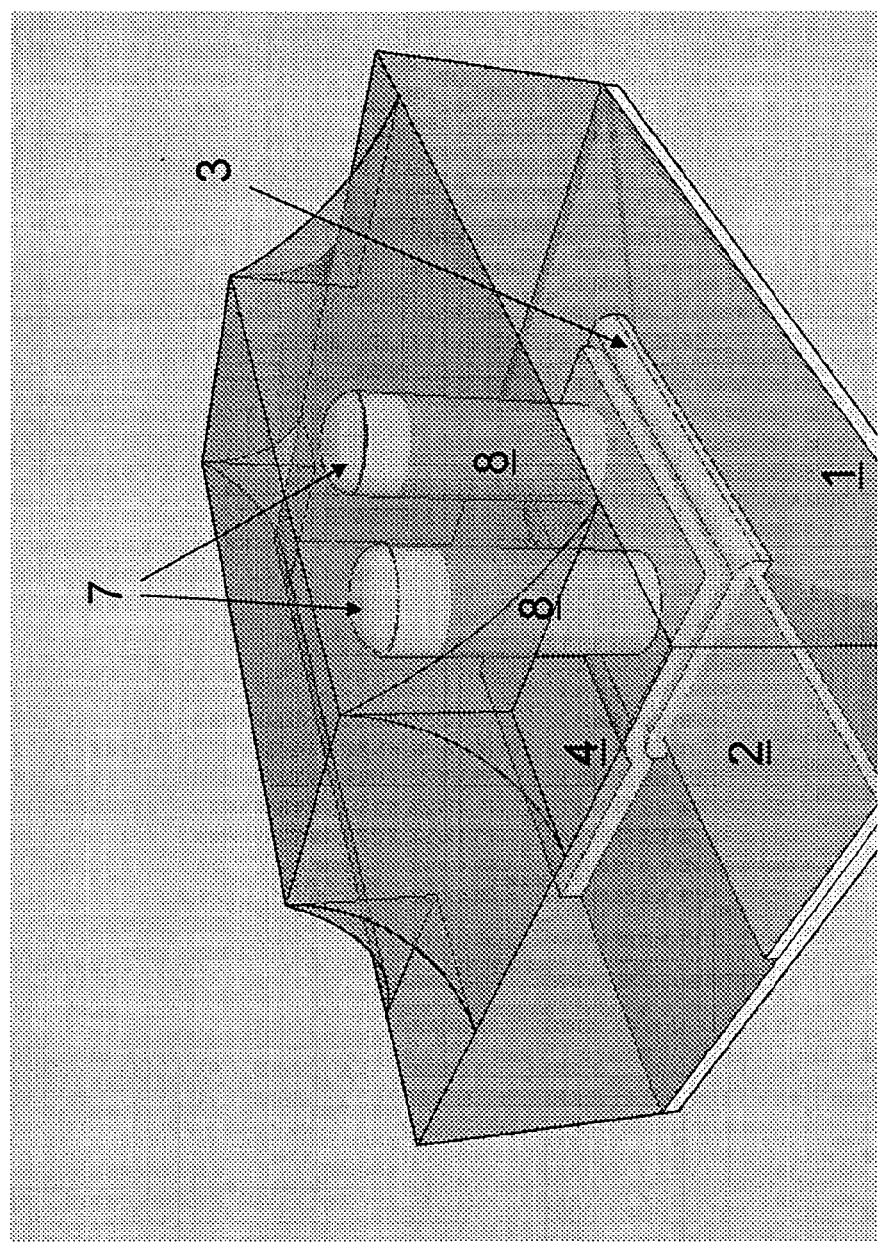

In a next step which is illustrated in FIG. 7, the nanowires 8 may be grown. In the example given, two nanowires 8 are grown. However, according to other embodiments, any number of nanowires 8 may be grown. The nanowires 8 may be formed of a same or similar material and may have a same or similar diameter and length. Examples of materials which may be used to form the nanowires 8 may be selected from group IV materials (e.g. Si, Ge, C) and binary compounds thereof, combinations of group III and group V materials (e.g. In, Ga, As, Sb, Al, P, B, N) and binary, tertiary and quaternary compounds thereof, combinations of group II and group VI materials (e.g. Cd, Zn, S, Se, Te, O) and binary, tertiary and quaternary compounds thereof and metal oxides. Examples of suitable materials that can be used with preferred embodiments may be GaAs, InP, ZnO, $GaAs_xP_y$, AlGaAs. The diameter of the nanowires 8 may be between 0.3 nm and 300 nm or may be lower than 100 nm, for example between 10 nm and 100 nm.

The nanowires 8 may be grown by any suitable technique known by a person skilled in the art such as e.g. chemical vapor deposition (CVD), Vapor Liquid Solid (VLS) or Vapor Solid Solid (VSS) techniques. Alternatively, nanowires 8 may be grown on a sacrificial substrate first and may then subsequently be transferred to the drain contact 4. The nanowires 8 may be doped, e.g. may be an n-type or p-type nanowire. According to preferred embodiments, the nanowires 8 may have a doping profile or, in other words, may have a changing dopant concentration along, for example, their longitudinal axis. Doping of the nanowires 8 may be performed during or after growth.

It has to be noted that, according to preferred embodiments, the nanostructures may also be nanotubes which may, for example, be carbon nanotubes (CNTs).

Figure 9:
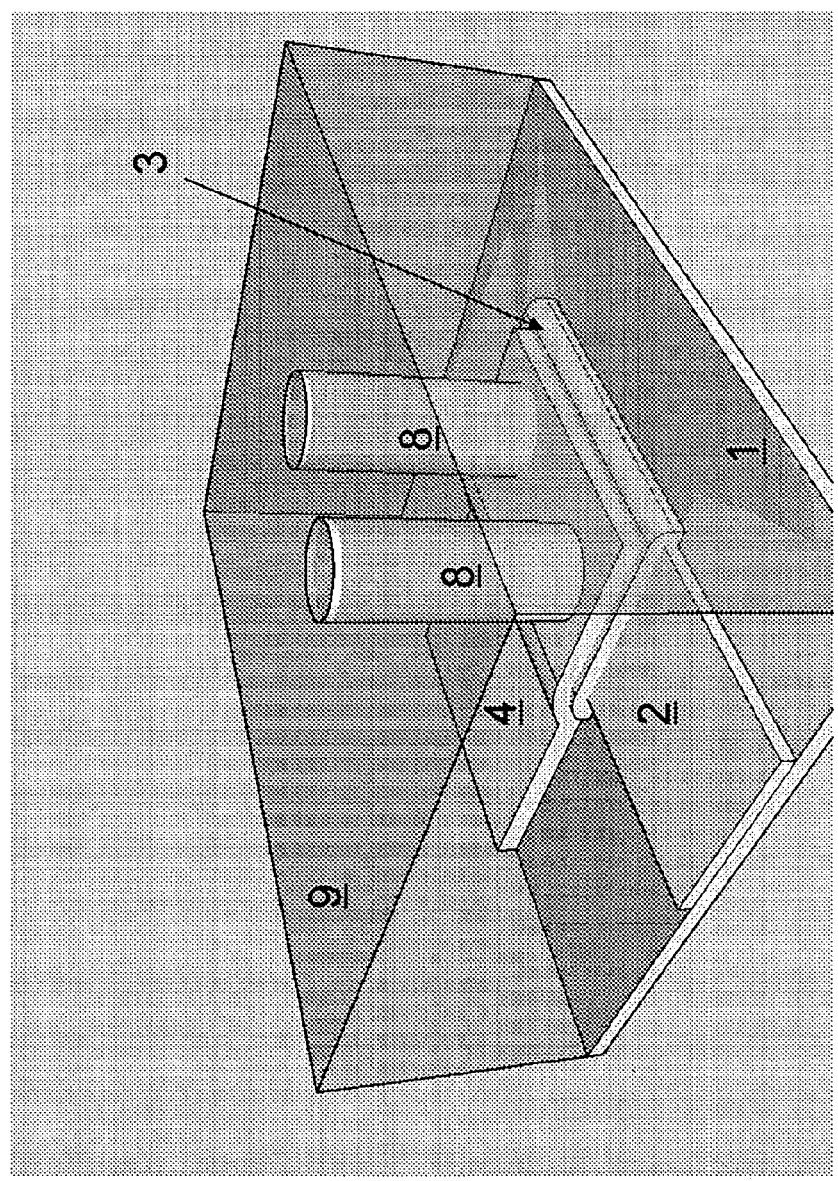
Figure 10:
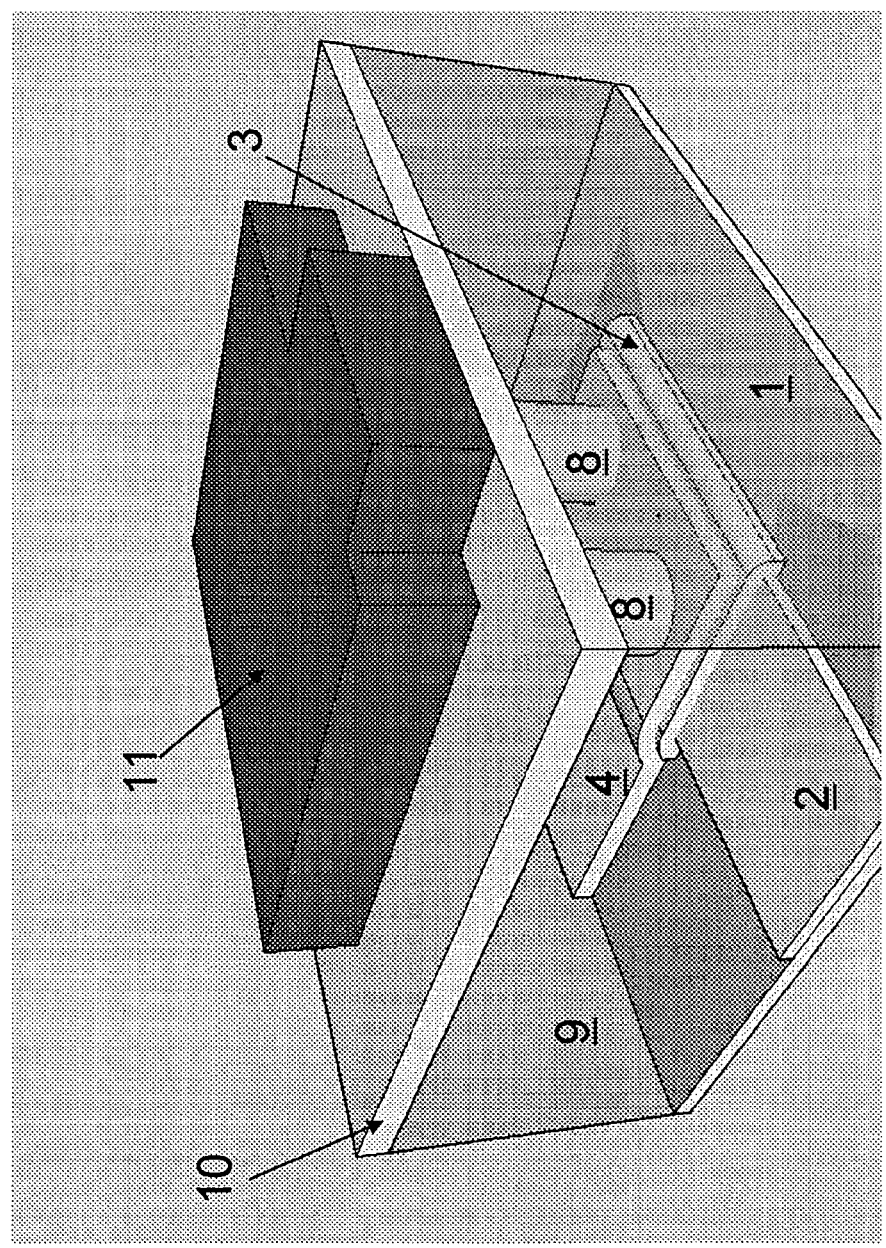

After growing the nanowires 8, a dielectric material 9 is provided and arranged so as to embed or, in other words, to surround the nanowires 8 (see FIG. 9). The dielectric material is chosen such that it is selectively permeable with respect to specific components, e.g. liquid or gas molecules, present in a fluid. A suitable dielectric material 9 to be used with preferred embodiments may be Nanoclustered Silica (NCS®). NCS is a spin-on dielectric material comprising a $SiO_2$ matrix with organic porogens which can provide selectivity (permeability). The dielectric material 9 may be provided by, for example, spin-on techniques. For example, the dielectric material 9 may be a low- or high-k dielectric material. Moreover, the dielectric material 9 may be any suitable dielectric material as long as its properties can be tuned to the nature of the component that has to be detected or measured. The dielectric material 9 may be porous dielectric material and/or may be an optically transparent material.

The dielectric material 9 may then be partly removed to expose an upper surface of the nanowires 8, such that when a second contact, in the example given a source contact 12, is provided, it makes direct contact with the nanowires 8 (see FIG. 9). Partially removing the dielectric material 9 may, for example, be done by polishing techniques, e.g. chemical mechanical polishing (CMP), or by etching techniques (etching back), as known by a person skilled in the art.

When, for example, a porous dielectric material 9 is used and CMP is used to partially remove it, CMP-slurry can penetrate into the porous dielectric material 9, implying that it may come in contact with the nanowires 8 and change their properties and that it will need to be removed from the dielectric material 9 afterwards. In order to avoid this penetration or exposure of the nanowires 8 to harmful process environments, a dielectric material 9 can be chosen which contains so-called "porogens" that can introduce pores into the dielectric material 9 after a heat treatment (thermal anneal), such that a 'non' porous dielectric material 9 is available during polishing while the porosity is created by a heat treatment after completion of the integration flow so that the porosity is created after exposure to harmful process environments. Alternatively, the CMP step, or in general the partial removal of the dielectric material 9, may be left out completely and the top of the nanowire 8 may be contacted by performing a CVD or ALD metal deposition step. In this case, metal precursors can penetrate into the dielectric material 9 to a sufficient depth in order to make contact to the metal catalyst particle 7 attached to the nanowire 8. Alternatively and in case the dielectric material 9 is thinner above the nanowires 8 than on the field areas, a partial etch-back can be considered for exposing the nanowires 8. This etch back process may enable selectively leaving the original metal catalyst particle 7 for top contacting because the catalyst particle 7 is not etched away, only the dielectric material 9 is. The composition of the etch plasma used for this purpose can be chosen such that only the dielectric material 9 is etched away and not the catalyst particle 7, as is known by a person skilled in the art.

The dielectric material 9 may also be substantially completely removed, e.g. etched out at the end of the process in order to fully expose the nanowires 8. This could be done, for example, to facilitate post-processing functionalization tests or to assess the mechanical stability or response of the sensor without dielectric material 9. It is clear that this is only done for experimental purposes as the sensor device 20 cannot operate if the dielectric material 9 is not present.

Next, a second contact, in the example given source contact 12, may be provided. Therefore, first a hardmask 10 and a top contact resist pattern 11 may be provided by e.g. conventional lithographic patterning (see FIG. 10). This may be done in order to minimize ash damage to the dielectric material 9 because the resist 11 can be removed before a pattern is etched into the dielectric material 9. Ash damage can occur when the resist 11 is, for example, acting as a hardmask because in that case the resist pattern 11 will still be present during etching and thus needs to be removed after etching. To remove the resist 11 an ashing process, also referred to as resist stripping, may be used. This ashing process may cause damage or leave residues on the etched dielectric material 9.

Figure 11:
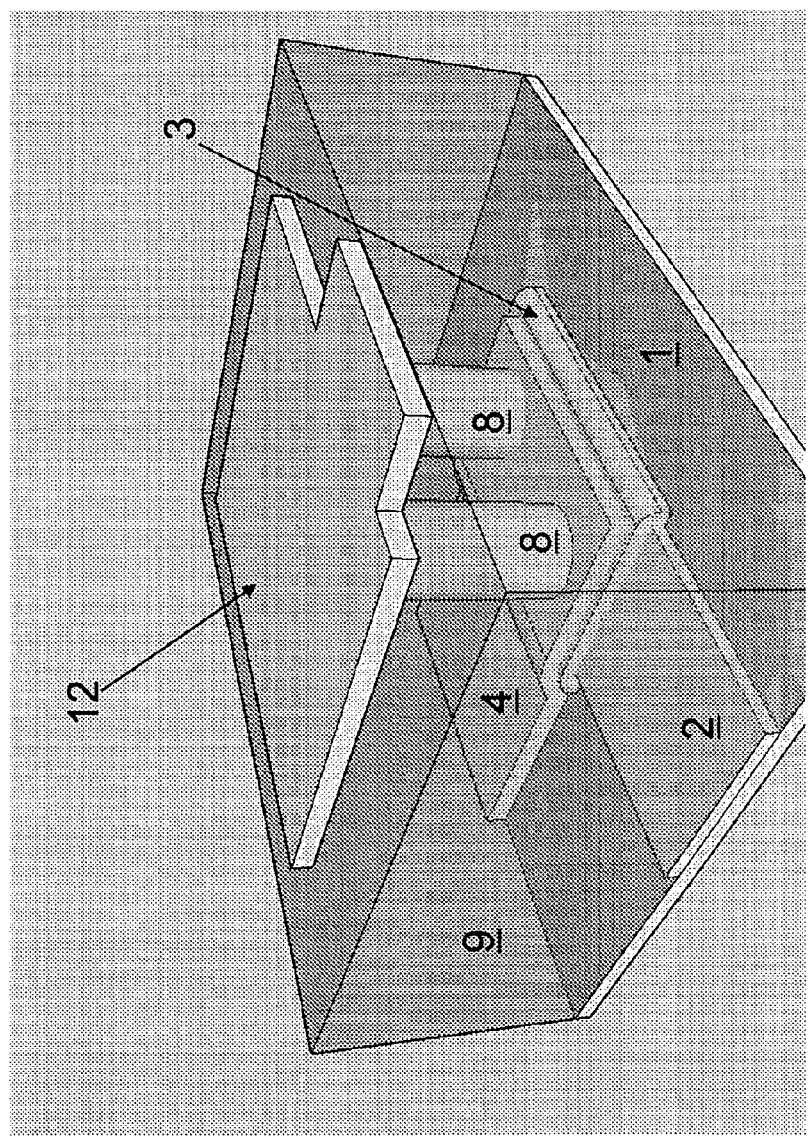
Figure 12:
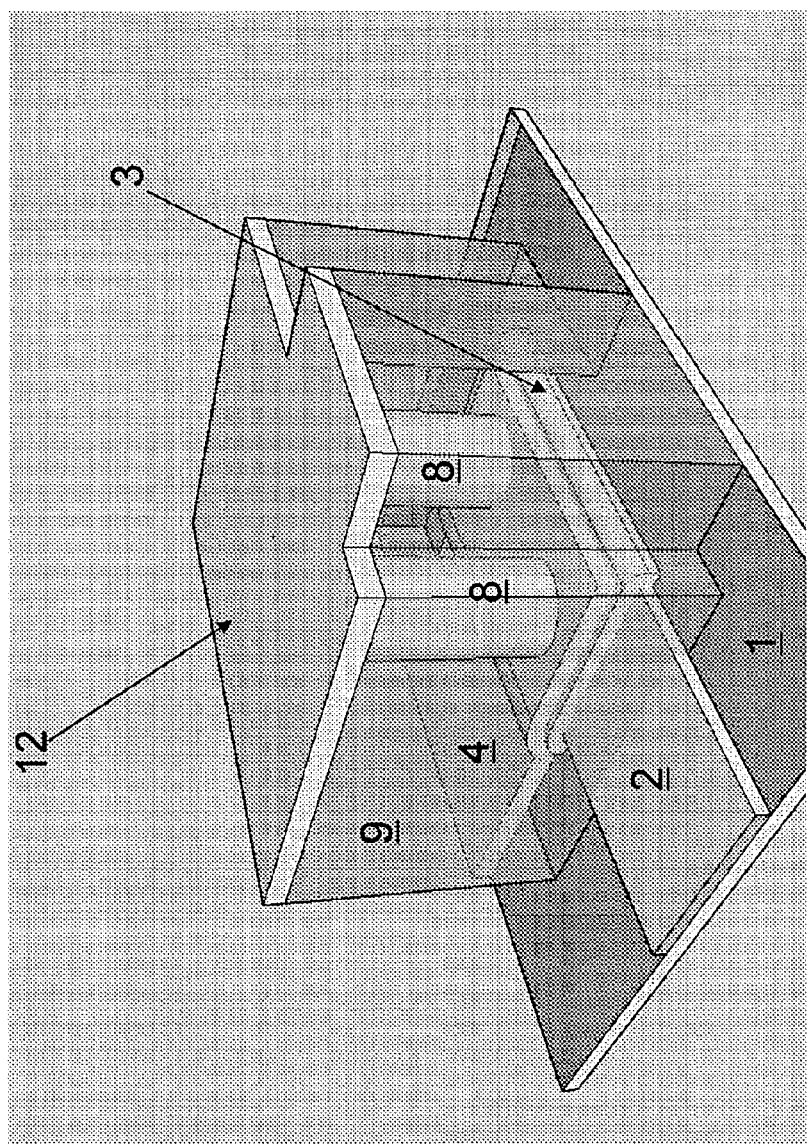

Next, the hardmask 10 is patterned according to the top contact resist pattern 11 to form the second contact, in the example given the source contact 12 (see FIG. 11). Subsequent, the dielectric material 9 is etched according to the pattern of the source contact 12 (see FIG. 12).

The material for forming the source contact 12 and the drain contact 4 may be chosen such that a good Ohmic contact is formed between the nanowire 8 and the source contact 12 while a Schottky contact is formed between the nanowire 8 and the drain contact 4.

Figure 13:
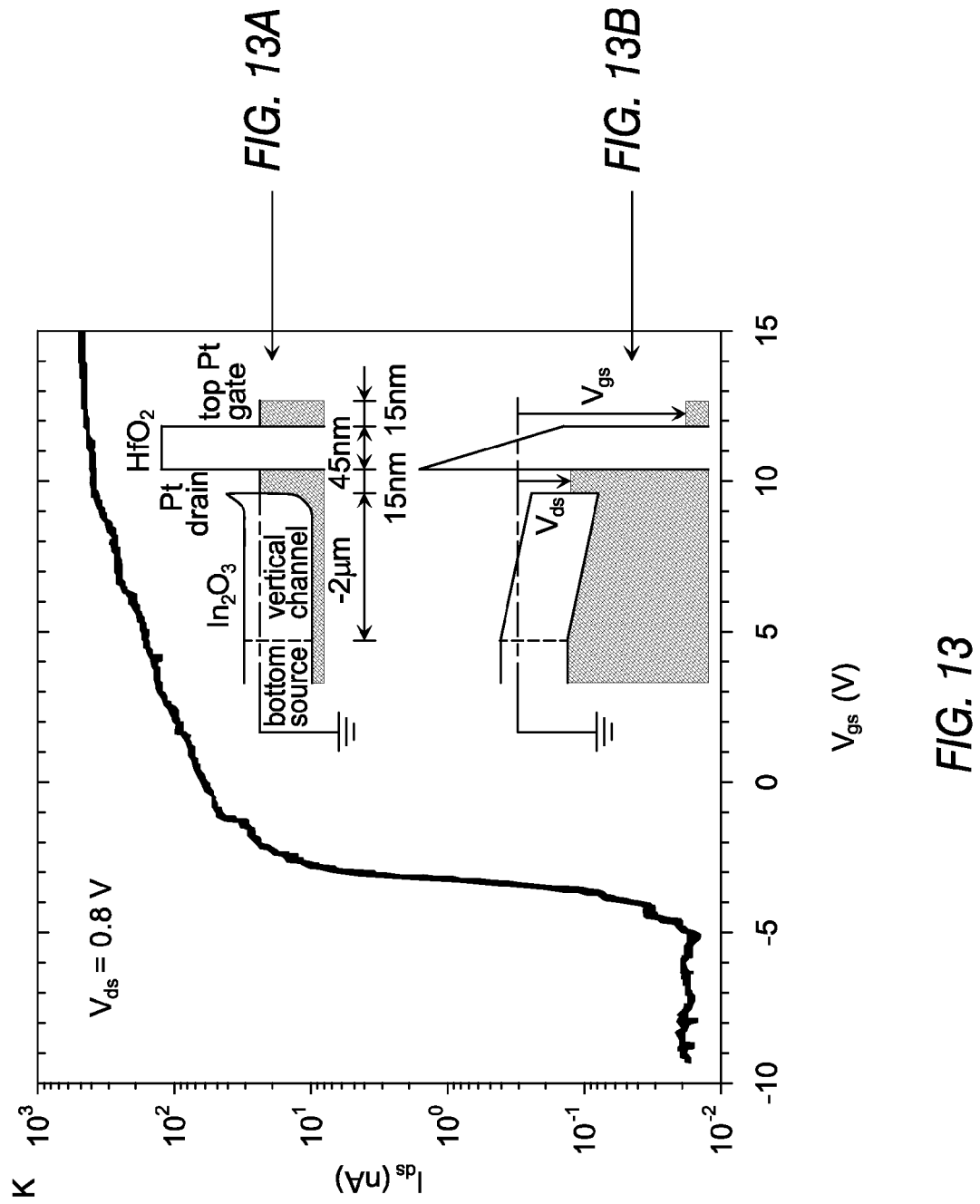
FIG. 13 shows a band diagram for a gate beyond drain field-effect transistor according to the prior art (as shown by Pho Ngyen et al. in Nanoletters 4, 651, 2004) in equilibrium (FIG. 13A) and in operation (FIG. 13B).

The method for manufacturing a sensor device 20 according to preferred embodiments may be based on a simplified integration process flow. The simplified integration process flow is obtained by placing the gate contact 2 beyond the drain contacts 4 such that the problem and the complexity of wrap-around gate contacts as described in current state of the art nanostructure devices is solved. FIG. 13 illustrates the band diagram for a gate beyond drain FET as shown by Pho Ngyen et al. (Nanoletters 4, 651, 2004). Transfer characteristics of such a FET are illustrated for a drain bias of Vds=0.8 V. FIG. 13A shows a band diagram of the FET in equilibrium with Vgs (gate bias)=Vds=0 V while FIG. 13B shows the FET in operation with Vgs>>Vds>0 V indicating that the drain bias accelerates the electrons while the gate bias modulates the electron density and also accelerates the electrons. It can therefore be concluded that a gate-beyond-drain FET can be used as an alternative to a wrap-around gate to tune a nanowire FET to close to the threshold voltage in order to maximize sensitivity to adsorbing gasses.

The method according to preferred embodiments for manufacturing a sensor device 20 may be performed using standard, state of the art equipment, while avoiding contamination issues during the fabrication process. To avoid possible contamination, e.g. originating from the catalyst used to initiate growth of the nanostructure, the gate contact 2 and drain contact 4 can be processed before fabrication of the nanowires 8 which has the additional advantage that the gate contact 2 and drain contact 4 can be connected directly to an underlying CMOS and/or interconnect structure. Alternatively, bondpads can be connected to the gate contact 2 and drain contact 4 for initial testing of the sensor device 20.

All references cited herein are incorporated herein by reference in their entirety. To the extent publications and patents or patent applications incorporated by reference contradict the disclosure contained in the specification, the specification is intended to supersede and/or take precedence over any such contradictory material.

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention as embodied in the attached claims.

What is claimed is:

1. A sensor device for determining at least one of a presence and an amount of at least one component in a fluid, the sensor device comprising:
at least one sensor unit on a substrate configured to be arranged in a fluid, wherein the sensor unit comprises at least one elongated nanostructure situated in a direction substantially perpendicular to the substrate and a dielectric material essentially surrounding the elongated nanostructure, wherein the elongated nanostructure has a bottom and a top and at least a first contact and a second contact, wherein the first contact is a drain contact and is connected to the bottom of the elongated nanostructure, and wherein the second contact is a source contact and is connected to the top of the elongated nanostructure, wherein the elongated nanostructure has a gate structure underneath the drain contact, wherein the dielectric material is selectively permeable for at least one component in the fluid, and wherein, in use, the elongated nanostructure is configured for sensing the component permeated through the dielectric material.

2. The sensor device of claim 1, comprising at least two sensor units, each sensor unit comprising elongated nanostructures having an essentially similar diameter and an essentially similar composition.

3. The sensor device of claim 1, comprising at least two sensor units, the sensor unit comprising elongated nanostructures that differ from each other in at least one of composition and diameter.

4. The sensor device of claim 1, comprising at least a first sensor unit and second sensor unit, wherein the dielectric material surrounding the elongated nanostructure of the first sensor unit differs in composition from the dielectric material surrounding the elongated nanostructure of the second sensor unit.

5. The sensor device of claim 1, wherein the gate structure comprises a gate contact and a gate dielectric, wherein the gate dielectric is situated in between the gate contact and the drain contact such that the gate contact and the drain contact do not contact each other.

6. The sensor device of claim 1, wherein the first contact and the second contact comprise a conductive material.

7. The sensor device of claim 1, wherein the elongated nanostructure has a diameter of from about 3 nm to about 300 nm.

8. The sensor device of claim 1, wherein the elongated nanostructure is functionalized to improve selectivity to the component to be detected.

9. The sensor device of claim 1, wherein the elongated nanostructure comprises a material selected from the group consisting of a group IV material, binary compounds of a group IV material, a group III-V material, binary compounds of a group III-V material, tertiary compounds of a group III-V material, quaternary compounds of a group III-V material, a group II-IV material, binary compounds of a group II-IV material, tertiary compounds of a group II-IV material, quaternary compounds of a group II-IV material, a metal oxide, and combinations thereof.

10. The sensor device of claim 1, wherein the elongated nanostructure is a nanowire or a carbon nanotube.

11. The sensor device of claim 1, further comprising a detector configured for measuring a change in a physical property of the elongated nanostructure upon adsorption of the component by the elongated nanostructure.

12. The sensor device of claim 11, wherein the detector is an electrical detector configured for measuring a change in electrical conduction of the elongated nanostructure.

13. The sensor device of claim 12, wherein the detector is an optical detector configured for measuring a change in electroluminescence of the elongated nanostructure.

14. The sensor device of claim 1, wherein the sensor device is a gas sensor configured for detecting a gas molecule present in a gas.

15. The sensor device of claim 1, wherein the sensor device is a liquid sensor configured for detecting a liquid molecule present in a liquid.

16. The sensor device of claim 1, wherein the dielectric material is an optically transparent dielectric material.

17. The sensor device of claim 1, wherein the dielectric material has a porosity configured to permit passage therethrough of the component.

18. The sensor device of claim 1, wherein the dielectric material has a pore size configured to permit passage therethrough of the component.

19. The sensor device of claim 1, wherein the dielectric material has a porosity and pore size configured to permit passage therethrough of the component.

20. The sensor device of claim 1, configured to distinguish between a plurality of different components on a basis of penetration velocity, wherein the sensor device comprises a plurality of sensor units, each sensor unit comprising a dielectric material having a unique penetration velocity.

21. The sensor device of claim 1, configured to distinguish between a plurality of different components on a basis of diffusion distance, wherein the sensor device comprises a plurality of sensor units, each comprising a dielectric material having a unique diffusion distance.

22. The sensor device of claim 1, wherein the component is a gas molecule.

23. The sensor device of claim 22, wherein the component induces a change in electrical conduction of the nanowire by absorbing to the nanowire.

24. The sensor device of claim 23, wherein the change in electrical conduction is indicative of a concentration of the component in the fluid.

25. The sensor device of claim 22, and wherein the component induces a change in electroluminescence of the nanowire by absorbing to the nanowire.

26. The sensor device of claim 25, wherein the change in electroluminescence is indicative of a concentration of the component in the fluid.

27. The sensor device of claim 1, wherein the component is a liquid molecule.

28. The sensor device of claim 27, wherein the component induces a change in electrical conduction of the nanowire by absorbing to the nanowire.

29. The sensor device of claim 28, wherein the change in electrical conduction is indicative of a concentration of the component in the fluid.

30. The sensor device of claim 27, wherein the component induces a change in electroluminescence of the nanowire by absorbing to the nanowire.

31. The sensor device of claim 30, wherein the change in electroluminescence is indicative of a concentration of the component in the fluid.

32. The sensor device of claim 1, wherein the component is a molecule dissolved in a solvent or in a mixture of solvents 33. The sensor device of claim 1, wherein the dielectric material is a high-k dielectric material.

34. The sensor device of claim 1, wherein the dielectric material is a low-k dielectric material.

35. The sensor device of claim 1, wherein the dielectric material is $HfO_2$.

36. The sensor device of claim 1, wherein the dielectric material is nanoclustered silica.

37. The sensor device of claim 1, wherein the dielectric material comprises porogens that introduce pores into the dielectric material after a thermal anneal.

* * * * *